United States Patent [19]

Stoss et al.

[11] Patent Number: 5,227,537
[45] Date of Patent: Jul. 13, 1993

[54] METHOD FOR THE PRODUCTION OF 6,12-DIHYDRO-6-HYDROXY-CANNABIDIOL AND THE USE THEREOF FOR THE PRODUCTION OF TRANS-DELTA-9-TETRAHYDROCANNABINOL

[75] Inventors: Peter Stoss, Illertissen; Peter Merrath, Memmingerberg, both of Fed. Rep. of Germany

[73] Assignee: Heinrich Mack Nachf., Illertissen, Fed. Rep. of Germany

[21] Appl. No.: 818,040

[22] Filed: Jan. 8, 1992

[30] Foreign Application Priority Data

Jan. 9, 1991 [DE] Fed. Rep. of Germany ....... 4100441

[51] Int. Cl.$^5$ ...................... C07C 33/36; C07C 43/21
[52] U.S. Cl. ................................... 568/811; 568/619; 568/620; 568/808; 568/809
[58] Field of Search ............... 568/743, 808, 809, 811, 568/619, 620

[56] References Cited

U.S. PATENT DOCUMENTS 3,656,906  4/1972  Bullock ........................ 568/743

OTHER PUBLICATIONS

Garrett et al., "Chemical Abstracts" vol. 88 (No. 22); p. 158340n (1978).
Stoss et al, "Chemical Abstracts," vol. 115 (No. 17) p. 183602h (1991).
Tetrahedron Letters No. 8, pp. 681–684 (1979) Hendrick et al., "Hashish:Synthesis of . . . ".

Primary Examiner—Werren B. Lone
Attorney, Agent, or Firm—Michael N. Meller

[57] ABSTRACT

A method is described for the production of 6,12-dihydro-6-hydroxy-cannabidiol which is obtained by the reaction of olivetol and cis-p-menth-2-ene-1,8,-diol and the reaction thereof to yield trans-delta-9-tetrahydrocannabinol.

17 Claims, No Drawings

METHOD FOR THE PRODUCTION OF 6,12-DIHYDRO-6-HYDROXY-CANNABIDIOL AND THE USE THEREOF FOR THE PRODUCTION OF TRANS-DELTA-9-TETRAHYDROCANNABINOL

Cannabinoid compounds are components which can be isolated from Cannabis spp. Due to its physiological activity trans-delta-9-tetrahydrocannabinol ($\Delta^9$-THC) is of substantial significance. This compound is also referred to as 6a,7,8,10a-tetradydro-6,6,9-trimethyl-3-pentyl-6H-dibenzo[b,d]pyran-1-ol.

The psychotropic but non-habit forming effects mean that this compound is of interest as pharmaceutical component.

The prior art discloses several different methods for the preparation of $\Delta^9$-THC. In conventional methods there is however the disadvantage that known synthesis paths lead to a number of by-products, which are very difficult to separate from the desired final product. Furthermore the final product is obtained in the form of a resinous mass, something that is hardly conducive to simple purification. Due to these disadvantages production on an industrial scale meets with substantial difficulties.

The compound 6,12-dihydro-6-hydroxy-cannabidiol described in the present application has so far not been either synthetically produced or used as an intermediate for the production of trans-delta-9-tetrahydrocannabinol. One reference to it in the literature (see Garrett et al., J. Pharm. Sci. 67 (1978) pages 27–32) only relates to the analytical chromatographic trace detection of one of a number of many other products of decomposition of delta-9-THC in an acidic solution. The compound has therefore not been produced in preparative quantities nor used for any sort of reactions. Furthermore the physical data of the compound have not been described previous to the present application.

One object of the present invention is therefore to provide a method for the production of trans-delta-9-tetrahydrocannabinol both with a sufficient purity and also on an industrial scale.

In order to achieve this object firstly trans-delta-9-tetrahydrocannabinol is produced as an intermediate, which may be readily purified by crystallization. This intermediate is then converted by ring condensation to the desired delta-9-THC.

The method of production in accordance with the invention will be made clear by the following reaction scheme:

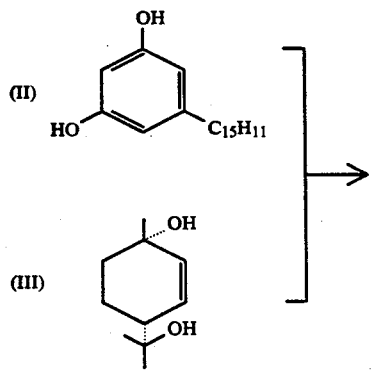

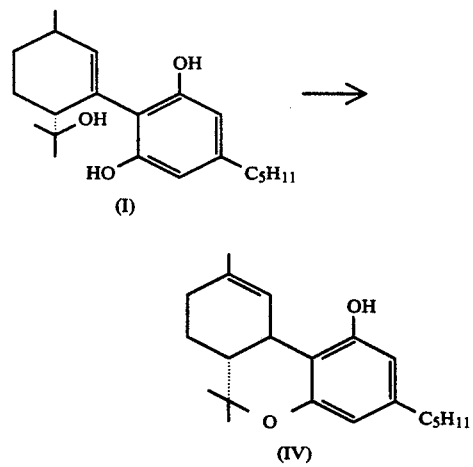

In accordance with the invention the first step is to produce the intermediate 6,12-dihydro-6-hydroxy-cannabidiol which may also be termed 1,3-dihydroxy-2-[6-(1-hydroxy-1-methyl-ethyl)-3-methyl-2-cyclohexene-1-yl]-5-pentyl-benzene. This compound is denoted I in the above scheme.

For the synthesis of 6,12-dihydro-6-hydroxy-cannabidiol as the intermediate in accordance with the invention the starting materials are the readily available olivetol (formula II) and cis-p-menth-2-ene-1,8-diol (formula III). The reaction is performed in a suitable solvent, aromatic hydrocarbons such as benzene and toluene, halogenated hydrocarbons such as methylene chloride, chloroform, dichloroethane and trichloroethane, ethers such as diethylether, diisopropylether and tetrahydrofuran having proved to be suitable. Furthermore it is possible to use mixtures of the said solvents.

Toluene, benzene, methylene chloride and chloroform are the preferred solvents for use in the method of the invention.

Preferably the reaction in accordance with the invention is performed in the presence of a suitable catalyst, proton acids such as for instance haloid acids, sulfuric acid, phosphoric acid, perchloric acid, organic sulfonic acids, such as for instance methanesulfonic acid and p-toluenesulfonic acid, carboxylic acids, such as for instance oxalic acid, trifluoroacetic acid and other Lewis acids, such for instance boron trifluoride, ferric chloride, zinc chloride, zinc bromide, stannic chloride, titanium chloride or iodine having proved to be suitable. Furthermore mixtures of the individual catalysts may be used in certain cases.

Preferably hydrochloric acid and p-toluenesulfonic acid are used in accordance with the invention.

The method may be performed at temperatures between approximately $-30°$ C. and $+50°$ C., temperatures between $0°$ C. and $20°$ C. being preferred.

The reaction times are dependent on the solvent, the catalyst used and the reaction temperature. In fact it is possible to use reaction times between a few minutes and several hours.

The intermediate product produced may then be readily further purified by recrystallization. In this respect the use of petroleum ether has turned out to be suitable for the recrystallization.

Ring condensation may be used to produce the trans-delta-9-tetrahydrocannabinol ($\Delta^9$-THC) from 6,12- dihydro-6-hydroxy-cannabidol. This reaction is performed in a suitable solvent with the use of suitable catalysts and water binding substances. The solvent is in the form of a hydrocarbon, as for instance hexane, heptane, cyclohexane, petroleum ether, aromatic hydrocarbons, such as for instance benzene, toluene, chorinated hydrocarbons, such as for instance methylene chloride, chloroform and dichloroethane. Preferably methylene chloride and chloroform are used. Furthermore mixtures of the solvents may be used.

As a catalyst for the ring condensation Lewis acids such as for instance zinc chloride, zinc bromide, boron trifluoride, ferric chloride, stannic chloride, titanium chloride or iodine are used, zinc chloride and zinc bromide having proved to be more particularly suitable.

Water binding substances such as neutral substances as for instance magnesium sulfate, sodium sulfate, calcium sulfate or molecular sieves may be used, the last-named having proved more particularly suitable.

The reaction is performed at a temperature between approximately $-20°$ C. and the boiling point of the corresponding solvent.

The reaction times are dependent on the catalyst, the solvent, the water binding substance and the reaction temperature. Dependent on the selected conditions times from a few minutes to several days are required.

For the man in the art it will be clear that the reactions in accordance with the invention may be also performed using such functionalized derivatives as may also be used for the synthesis of $\Delta^9$ THC.

It is an advantage in the method in accordance with the invention that starting with readily available materials the intermediate product in the form of 6,12-dihydro-6-hydroxy-cannabidiol may be produced simply with a good yield and that such product may be purified without any great difficulty.

Starting with the intermediate product in accordance with the invention it is possible to obtain highly pure, that is to say low-isomer $\Delta^9$ THC, the purification of the THC so obtained being possible by simple elution of a silica gel column. With the aid of the method described above it is possible to achieve a high, reproducible yield of the $\Delta^9$ THC and the production of the final product is also possible on an industrial scale.

EXAMPLE 1

The production of 6,12-dihydro-6-hydroxy-cannabidiol.

90 g of olivetol were agitated with 85 g of cis-p-menth-2-ene-1,8,-diol and 4 g of p-toluenesulfonic acid.-$H_2O$ in 4 l methylene chloride for 24 hours at 20° C. Then extraction was performed once with 200 ml. of 4% calcium carbonate solution and the organic phase was reduced in vacuum to an oil. In this respect approximately 170 g of residue were obtained, which were dissolved in 1 l of petroleum ether (50/70) and extracted three times with respectively 300 ml of 0.5 N sodium hydroxide.

The petroleum ether phase was then run into a silica gel column (approximately 500 g of silica gel) and eluted with a mixture of petroleum ether (50/70) and diisopropylether (2:1). The eluate was reduced in volume under vacuum and the residue (approximately 102 g) was recrystallized from 600 ml of petroleum ether (50/70). 77 g of the desired product were obtained. The characteristic data of the 6,12-dihydro-6-hydroxy-cannabidiol were as follows:

Fusion point: 77° to 77.5° C.

Optical rotation: $[\alpha]_D^{20} = -70.3°$ C. (c=1.00; CHCl$_3$)
UV spectrum: (UV)$\lambda_{max}$ (ethanol 95%) 275 nm ($\epsilon$1024) $\lambda_{max}$ (ethanol 95%) 281 nm ($\epsilon$987)

Infrared spectrum: (IR, KBr pellet) [cm]$^{-1}$ 3392, 2956, 2930, 2859, 1630, 1582, 1446, 1379, 1369, 1335, 1308, 1231, 1202, 1186, 1158, 1076, 1046, 1028.

Mass spectrum: (MS 70 eV, EI) m/z 332(M+, 10), 314(29), 299(37), 297(10), 286(12), 271(44), 258(13), 246(11), 243(13), 231(100), 193(25), 174(12), 137(14), 93(18), 59(25), 43(63); TMS derivative: m/z 548 (M+).

Nuclear magnetic resonance: ($^1$H-NMR, 60 MHz, CDCl$_3$) $\delta$(ppm) 0.88 (tr, 3H, CH$_3$-18), 1.25 (s, 6H, CH$_3$-12), 1.30 (m, 4H, CH$_2$-17, CH$_2$-16), 1.57 (m, 2H, CH$_2$-15), 1.70 (m, 1H, CH-7$\alpha$), 1.80 (s, 3H, CH$_3$-11), 1.90 (m, 1H, CH-6a), 1.97 (m, 1H, CH-7$\beta$), 2.09 (m, 2H, CH$_2$-8), 2.44 (dd, 2H, CH$_2$-14), 3.85 (m, 11H, CH-10a), 5.66 (m, 1H, CH-10), 6.37 (s, 2H, arom. H).

Capillary gas chromatography: (KGC, J & W DB5-15N, 60° to 250° C., 5° /min.+30 min. isotherm.; relative retention time [RRT]).

| | |
|---|---|
| n-Hexadecane | RRT 1.000 |
| Sample A of 6,12-dihydro-6-hydroxy-cannabidiol | RRT 2.121 |
| Sample B of 6,12-dihydro-6-hydroxy-cannabidiol (TMS derivative) | RRT 1.946 |

EXAMPLE 2

Production of trans-delta-9-tetrahydrocannabinol.

10 g of 6,12-dihydro-6-hydroxy-cannabidiol were dissolved in 300 ml of methylene chloride and held for 24 hours under reflux in the presence of 20 g of zinc bromide and 15 g of molecular sieve 3 Å. Then filtration was performed and the filtrate reduced in volume. The residue was taken up in 100 ml of petroleum ether and run into a silica gel column (approximately 100 g of the gel). Then elution was performed with petroleum ether and the eluate was reduced in volume. The residue obtained was $\Delta^9$-THC with a purity of $\geq 96\%$.

We claim:
1. A method of producing 6,12-dihydrohydroxy-cannabidiol of the formula (I)

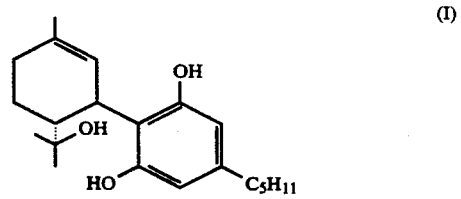

(I)

wherein an equimolar amount of olivetol of the formula (II)

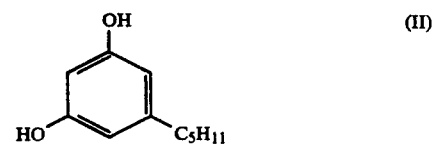

(II)

is reacted with cis-p-menth-2-ene-1,8-diol of the formula (III)

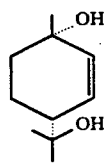
(III)

in an organic solvent in the presence of a Lewis acid catalyst.

2. The method as claimed in claim 1, wherein the solvent is selected from the group consisting essentially of aromatic hydrocarbons, halogenated hydrocarbons, ethers, and mixtures thereof.

3. The method as claimed in claim 2, wherein the solvent is selected from the group consisting essentially of toluene, benzene, methylene chloride and chloroform, and mixtures thereof.

4. The method as claimed in claim 1, wherein a protein acid, an organic sulfonic acid or another Lewis acid is used as a catalyst.

5. The method as claimed in claim 4, wherein the catalyst is hydrochloric acid or p-toluenesulfonic acid.

6. The method as claimed in claim 1, wherein the 6,12-dihydro-6-hydroxy-cannabidiol is further purified by crystallization from petroleum ether.

7. A method for producing trans-delta-9-tetrahydrocannabidiol of the formula (IV)

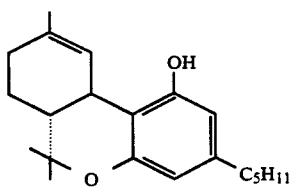
(IV)

wherein a ring condensation is performed on 6,12-dihydro-6-hydroxy-cannabidiol of the formula (I)

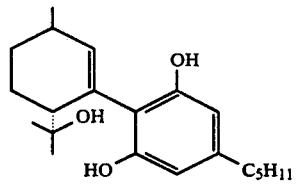
(I)

in a solvent selected from the group consisting essentially of hydrocarbons, aromatic hydrocarbons and chlorinated hydrocarbons and in the presence of a Lewis acid as a catalyst.

8. The method as claimed in claim 6, wherein said solvent is selected from the group consisting essentially of methylene chloride and chloroform.

9. The method as claimed in claim 1, wherein the catalyst is selected from the group consisting essentially of zinc chloride and zinc bromide.

10. The method as claimed in claim 7, wherein the ring condensation is performed in the presence of a water binding substance.

11. The method as claimed in claim 10, wherein the water binding substance is a molecular sieve.

12. The method as claimed in claim 2, wherein a protein acid, an organic sulfonic acid or another Lewis acid is used as a catalyst.

13. The method as claimed in claim 3, wherein a protein acid, an organic sulfonic acid or another Lewis acid is used as a catalyst.

14. The method as claimed in claim 2, wherein the 6,12-dihydro-6-hydroxy-cannabidiol is further purified by crystallization from petroleum ether.

15. The method as claimed in claim 3, wherein the 6,12-dihydro-6-hydroxy-cannabidiol is further purified by crystallization from petroleum ether.

16. The method as claimed in claim 4, wherein the 6,12-dihydro-6-hydroxy-cannabidiol is further purified by crystallization from petroleum ether.

17. A method according to claim 1, wherein the reaction product is further purified by crystallization.

* * * * *